(12) United States Patent
Dörschug et al.

(10) Patent No.: US 6,875,589 B1
(45) Date of Patent: Apr. 5, 2005

(54) MINI-PROINSULIN, ITS PREPARATION AND USE

(75) Inventors: Michael Dörschug, Bochum (DE); Paul Habermann, Eppstein/Taunus (DE); Gerhard Seipke, Hofheim am Taunus (DE); Eugen Uhlmann, Glashütten/Taunus (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 1826 days.

(21) Appl. No.: 08/402,394

(22) Filed: Mar. 10, 1995

Related U.S. Application Data (63) Continuation of application No. 08/080,060, filed on Jun. 23, 1993, now abandoned, which is a continuation of application No. 07/369,686, filed on Jun. 21, 1989, now abandoned.

(30) Foreign Application Priority Data

Jun. 23, 1988 (DE) ........................ P 38 21 159

(51) Int. Cl.⁷ .......................... C12N 15/17; C12N 1/16; C12N 1/21; A61K 38/28
(52) U.S. Cl. .................... 435/69.7; 435/69.1; 435/69.4; 435/243; 435/254.2; 530/303; 530/305; 536/23.4; 536/23.5; 536/23.51
(58) Field of Search ................. 530/303, 305, 530/350, 402; 514/3; 536/23.4, 23.5, 23.51; 435/69.1, 69.4, 69.7, 240.2, 255, 252.3, 252.33, 320.1

(56) References Cited

U.S. PATENT DOCUMENTS

| | | | |
|---|---|---|---|
| 4,608,364 A | | 8/1986 | Grau .............................. 514/4 |
| 4,916,212 A | * | 4/1990 | Markussen et al. ......... 530/303 |
| 4,946,828 A | * | 8/1990 | Markussen ..................... 514/3 |
| 5,149,716 A | * | 9/1992 | Vertesy et al. ................. 514/3 |
| 5,164,366 A | * | 11/1992 | Balschmidt et al. ........... 514/3 |
| 5,177,058 A | * | 1/1993 | Dorschug ...................... 514/4 |

FOREIGN PATENT DOCUMENTS

| | | |
|---|---|---|
| EP | 0 055 945 | 1/1981 |
| EP | 0 163 529 | 12/1985 |
| EP | 0 195 691 | 9/1986 |

OTHER PUBLICATIONS

R. Wetzel et al., Gene 16, pp. 63–71 (1981).

* cited by examiner

Primary Examiner—Christine J. Saoud
(74) Attorney, Agent, or Firm—Finnegan, Henderson, Farabow, Garrett & Dunner, L.L.P.

(57) ABSTRACT

A mini-proinsulin, in which the amino acid Arg bridges the A and the B chain instead of the C chain, shows insulin activity and is suitable for the preparation of pharmaceuticals for the treatment of diabetes mellitus. It can furthermore be converted into an insulin derivative simply using trypsin, the B chain of which is lengthened by Arg. This can be converted into insulin using carboxypeptidase B. Advantageously, however, the mini-proinsulin can also be converted to insulin directly in a one-pot process.

10 Claims, 6 Drawing Sheets

MINI-PROINSULIN, ITS PREPARATION AND USE

This application is a continuation of application Ser. No. 08/080,060, filed Jun. 23, 1993, now abandoned, which is a continuation of application Ser. No. 07/369,686, filed Jun. 21, 1989, abandoned.

The invention relates to a novel "mini-proinsulin" in which the unshortened B chain is only bonded to the A chain via an arginine residue. Human insulin is accessible from this mini-proinsulin without difficult chemical reaction.

Mini-proinsulins having a shortened C chain are known. Thus R. Wetzel et al., Gene 16 (1981), 63–71 have described a proinsulin having a C chain shortened to six amino acids. In the European patent application having the publication number (EP-A) 0,055,945, corresponding proinsulins are disclosed, the C chain of which is shortened to two amino acids.

In EP-A 0,163,529, insulin precursors having a shortened B chain are disclosed in which the C chain is either missing completely or else shortened to one amino acid. These precursors are converted into mature human insulin by trypsin-catalysed transpeptidation using an α-threonine ester.

On the other hand, the invention relates to human Des-(32–65) proinsulin or mini-proinsulin of the formula I $$B(1-30)\text{-Arg-}A(1-21) \tag{I},$$

in which B(1–30) and A(1–21) denote the B and A chain of human insulin. This compound is used not only as an intermediate for the preparation of human insulin $\text{Arg}^{B31}$-OH, called "mono-Arg-insulin" in the following, which has been disclosed in European Patent Nos. (EP-B) 0,132,769 and 0,132,770, and of human insulin, but it also shows a certain insulin activity its lf.

The invention therefore also relates to the compound of the formula I for use as a pharmaceutical, in particular for the treatment of diabetes mellitus, and furthermore pharmaceuticals containing the compound of the formula I, and pharmaceuticals composed of a pharmacologically acceptable excipient and the compound of the formula I.

The invention furthermore relates to the use of the compound of the formula I for the preparation of the mono-Arg insulin of the formula II (II)

in which A(1–21) and B(1–30) have the meanings mentioned previously and the -S-S-bridges are arranged as in insulin, and of human insulin by enzymatic cleavage. The immediate-conversion of the compound of the formula I into insulin in a "one-pot reaction" is particularly advantageous.

The invention furthermore relates to a process for the preparation of the compound of the formula I which comprises expressing a gene structure encoding for this compound in a host cell, preferably in a bacterium such as E. coli or in a yeast, in particular Saccharomyces cerevisiae, and, if the gene structure encodes for a fusion protein, liberating the compound of the formula I from this fusion protein. The invention relates in addition to DNA sequences which encode for the compound of the formula I, gene structures or plasmids which contain this DNA, and host cells, in particular bacteria such as E. coli or yeast cells, particularly yeasts of the strain Saccharomyces cerevisiae which contain such gene structures or plasmids. The invention furthermore relates to fusion proteins which contain a compound of the formula I, preferably fusion proteins in which the compound of the formula I is bonded via the bridging member -Met-Ile-Glu-Gly-Argto the "ballast component" of the fusion protein.

Further preferred embodiments of the invention are explained in more detail in the following.

Figure 1:
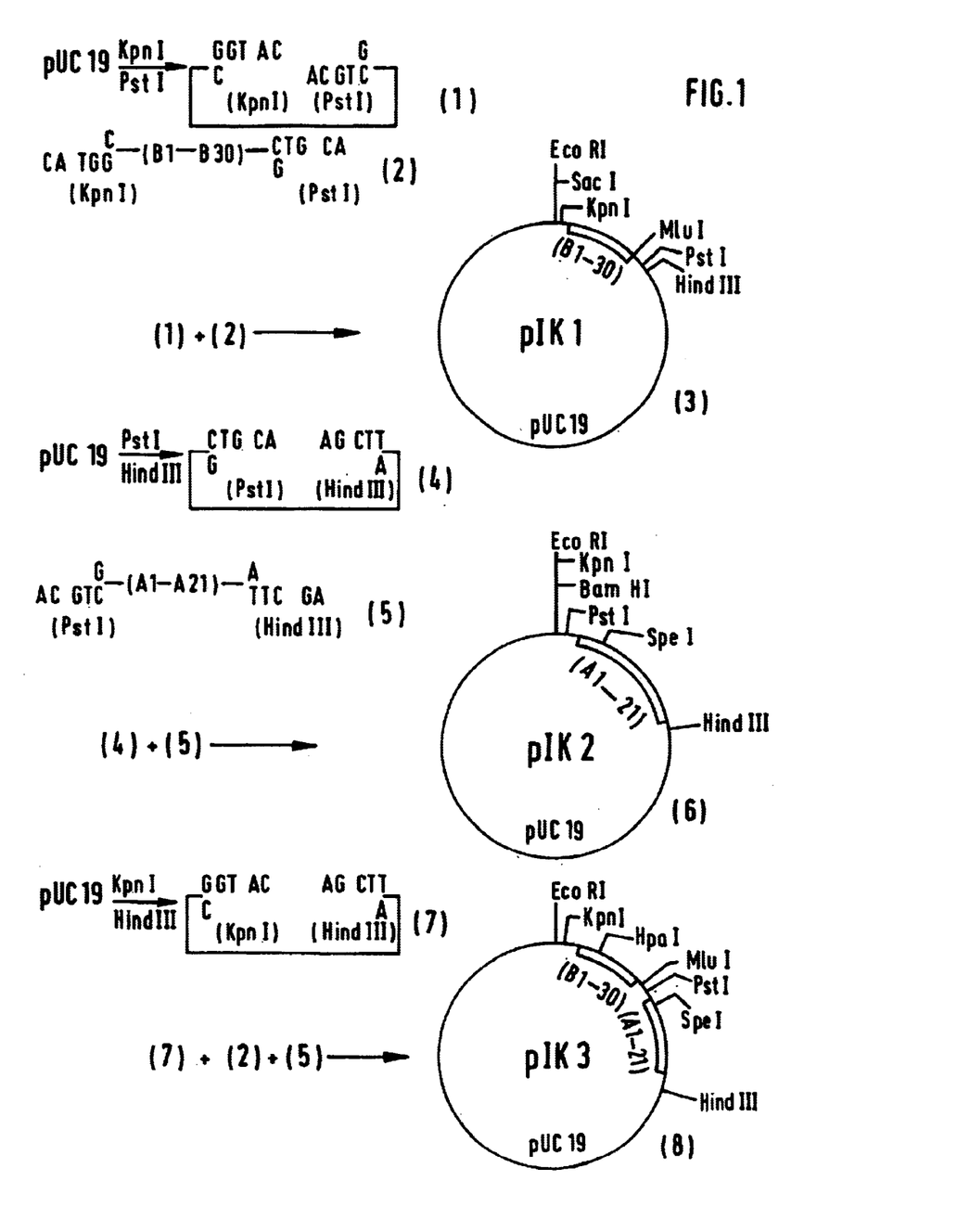
FIG. 1, FIG. 1a, and FIG. 1b show the construction of the *E.coli* expression vectors PIK10 and pSW3
Figure 1A:
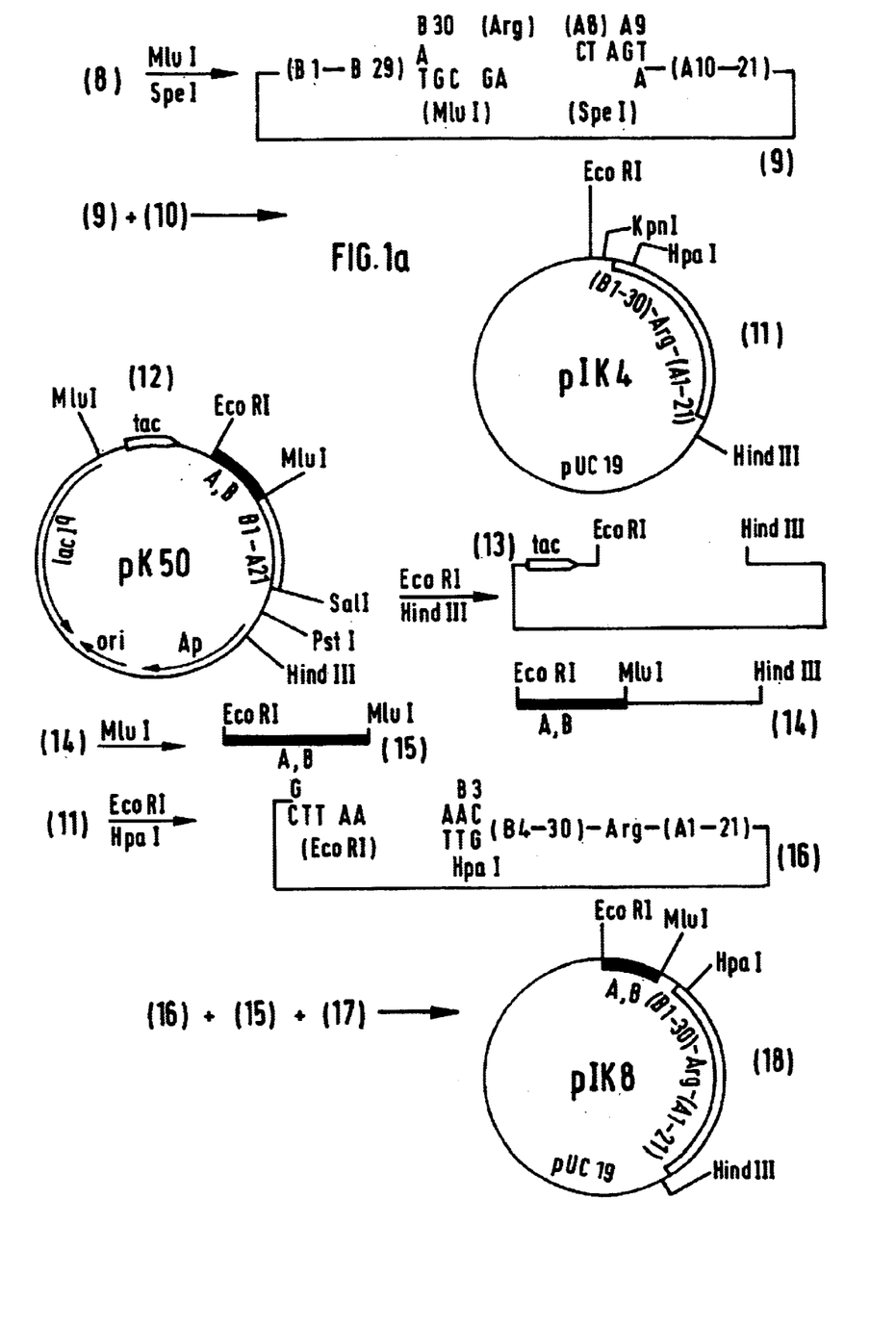
Figure 1B:
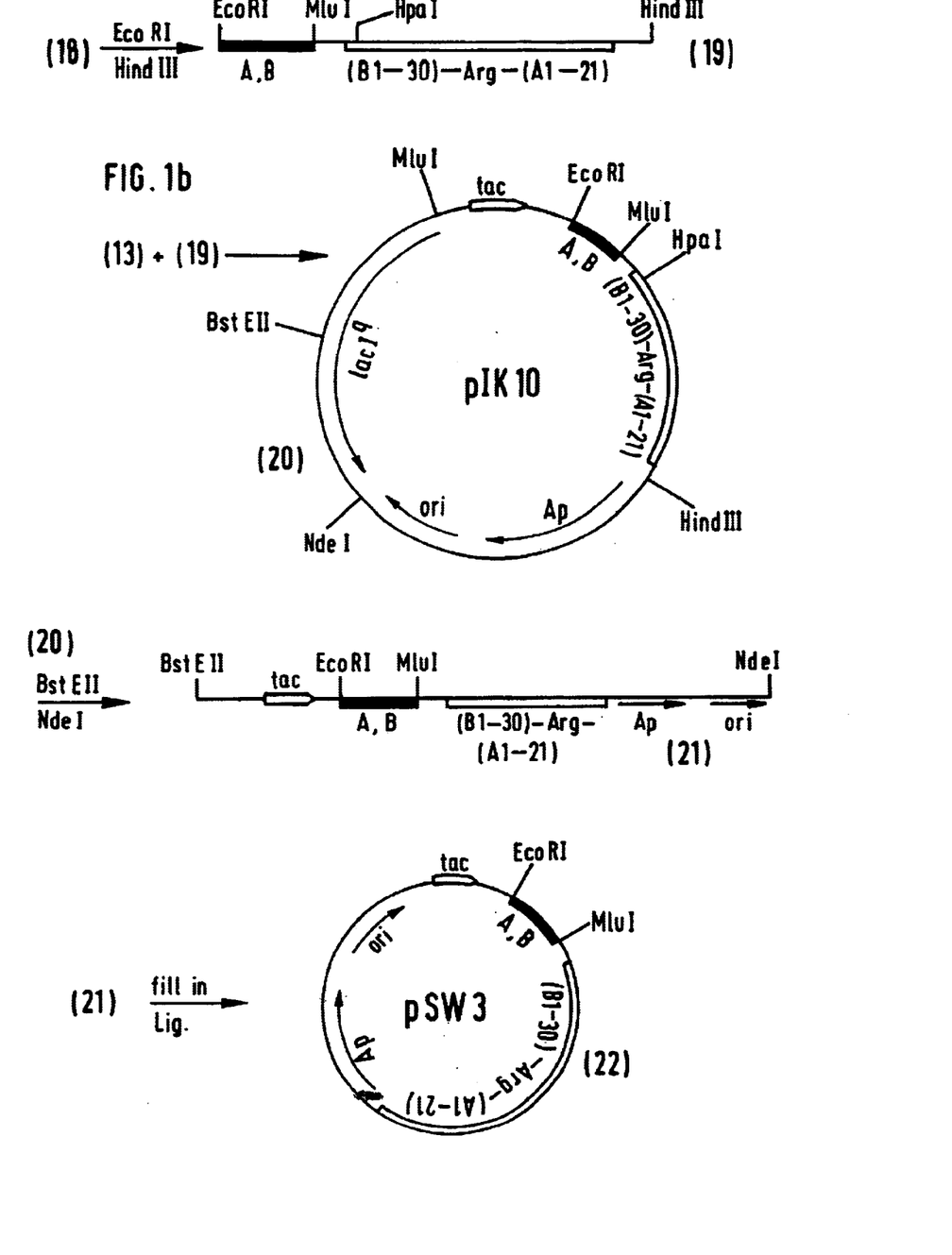
Figure 2:
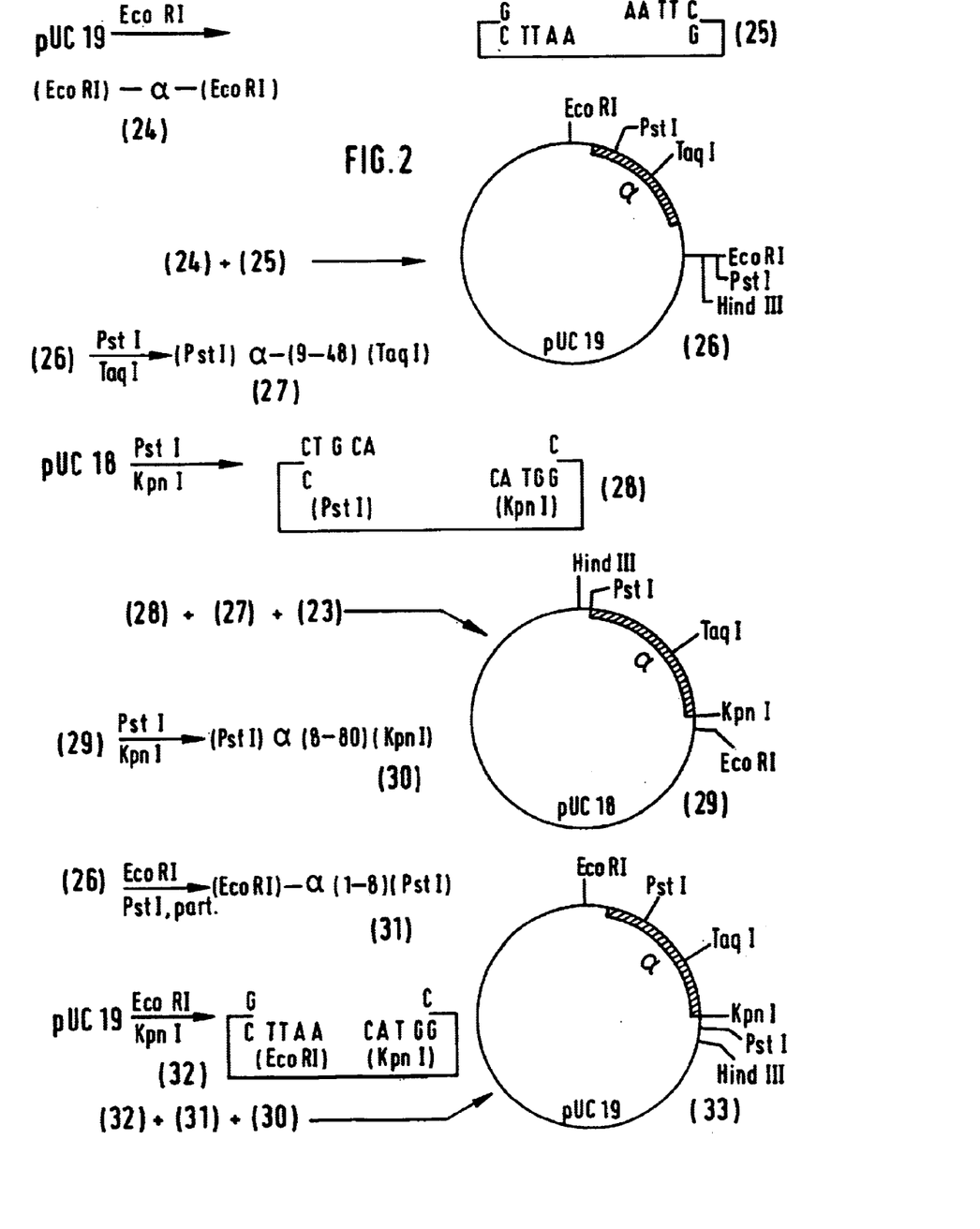
FIG. 2, FIG. 2a, and FIG. 2b show the construction of yeast expression vector pβfB102 and pαfB104.

The figures are used to explain the Examples, FIG. 1 (and its continuation in FIGS. 1a and 1b) showing the construction of the E. coli expression vectors PIK10 and pSW3 and FIG. 2 (and its continuation in FIGS. 2a and 2b) showing that of the yeast expression vector pαfB102 or pαfB104. These vectors encode for mini-proinsulin.

It has been found that the mini-proinsulin has the correct folding so that mono-Arg insulin is formed almost quantitatively after cleavage with trypsin. A surprisingly simple process for the preparation of mono-Arg insulin thus results. Human insulin can be prepared from this in a manner known per se. Mono-Arg insulin is furthermore used as an active compound in pharmaceuticals (EP-B 0,132,769).

The expression vector pK50 was described in EP-A 0,229,998 or in the corresponding AU-A 66,760/86. Mini-proinsulin can be prepared in a bacterium such as E. coli in the form of a fusion protein corresponding to this construction.

The poorly soluble fusion protein can be concentrated by washing with neutral buffer solutions. The mini-pro-insulin is liberated by cyanogen halide cleavage (E. Gross and B. Wittkop, J. Am. Chem. Soc. 82 (1961) 1510–1517). This still does not exist in the biologically active form, but consists of a non-uniform mixture having various inter- and intramolecular disulfide bridges, possibly also with other protein fragments. The S-sulfonate form of the molecule is prepared as a chemically uniform, relatively stable derivative (P. G. Katsoyannis et al., Biochemistry 6 (1967) 2635–2641). This derivative can be purified very easily by ion exchange chromatography and is an approved starting material for the folding into the native spatial structure with the formation of the correct disulfide bridges (Y. C. Du et al., Sci. Sin. 15 (1965) 229–236; H. P. Gattner et al., Hoppe-Seylers Z. physiol. Chem. 362 (1981) 1943–1049; B. H. Frank et al. in: "Peptides: Synthesis-Structure-Function", D. H. Rich and E. Gross, Publishers, (1981) 1043–1049). The success of this folding is safeguarded by HPLC analysis of the fragments resulting after cleavage with S. aureus protease V8 (U. Grau, Diabetes 34 (1985) 1174–1180).

The liberation of mono-Arg insulin or insulin by the action of trypsin or carboxypeptidase B or by enzymes having the same action (W. Kemmler et al., J. Biol. Chem. 246 (1971) 2780–2795) proceeds in a decidedly uncomplicated manner, since it proves particularly advantageous for this purpose that the number of possible cleavage sites is reduced compared to normal proinsulin. Because of this, the cleavage is considerably more simple to control (with respect to the formation of side products as in the preparation of Des-B30 insulin or Desocta-B23–B30 insulin). Both mono-Arg insulin and also insulin can be isolated in a known manner in highly pure form by ion exchange chromatography. The formation of the insulin and the mono-Arg derivative, the course of the purification and the quality of the final product are checked using customary RP-HPLC methods (G. Seipke et al., Angew. Chem. 98 (1986) 530–548).

Surprisingly, hardly any insulin Des-B30 is formed in the cleavage of mini-proinsulin in contrast to natural proinsulin.

Since the latter can only be separated from insulin in a very difficult manner, the "two-pot reaction" is preferred in the production of insulin from natural proinsulin, i.e. the principal products of the tryptic cleavage, insulin-Arg$^{B31}$–Arg$^{B32}$ and mono-Arg insulin are first separated from insulin Des-B30 via ion exchangers in a known manner and then cleaved to give human insulin by means of carboxypeptidase B (EP-B 0,195,691). In comparison, mini-proinsulin can be converted to human insulin in an ideal manner in a "one-pot reaction" simultaneously using trypsin and carboxypeptidase B or by means of enzymes having the same action.

The expression of the compound of the formula I in yeast with subsequent secretion is particularly advantageous, since the correctly folded proinsulin derivative can be isolated directly. Yeasts are used as host systems, as are shown, for example, in EP-A 0,248,227, thus for example *B. Pichia pastoris, Hansenula polymorphis, Schizosaccharomyces pombe* or, preferably *Saccharomyces cerevisiae*.

Vectors for expression in yeasts are known in large numbers. The preparation of the insulin derivative according to the invention is described in the following with the aid of the yeast α-factor system which, however, is only to be taken as an example, since other expression systems can also be employed in a manner known per se.

The structure of the yeast pheromone gene MFα is known from the publication Rurjan and Herskovitz, Cell 30 (1982) 933–943, where the possibility of the expression of other genes and the secretion of the gene products are also discussed. Regarding this, reference can also be made to Brake et al., Proc. Natl. Acad. Sci. USA 81 (1984), 4642–4646.

Alternatively, a yeast "Killertoxin" system can be used, or secretion via the acidic phosphatase or invertase system can be utilized.

As yeast vectors, so-called "shuttle" vectors are advantageously used which have a bacterial plasmid and a yeast plasmid replication origin and also a gene or genes for selection in both host systems. In addition, such vectors contain the promoter sequences necessary for the expression of foreign genes and, if appropriate, a terminator sequence to improve the yield so that the heterologous gene—expediently fused to secretory signals—is arranged between promotor and terminator. Such vectors are described, for example, in U.S. Pat. No. 4,766,073.

The genetic code is, as is known, "degenerate", i.e. a single nucleotide sequence encodes only for two amino acids, while the residual 18 encodable amino acids are allocated two to six triplets. For the synthesis of the gene for mini-proinsulin, there is thus a large variety of codon combinations to be chosen. It has now been found that the DNA sequence I encoding for mini-proinsulin (which is reproduced in the Appendix in the form of the two gene fragments IK I (Table 1) and IK II (Table 2)) is particularly advantageous, since it is optimized to codon use of both yeast and *E. coli*.

A "protruding" DNA sequence corresponding to the restriction endonuclease KpnI is situated at the 5' end of the encoding strand of the DNA sequence I. In comparison, the single-stranded sequence corresponding to the restriction enzyme HindIII is protruding at the 3' end of the encoding strand. These two different recognition sequences ensure the insertion of the DNA sequence I into plasmids in the desired orientation. Two translation/termination codons (stop codons) follow triplet No. 65 for asparagin in the encoding sequence. An internal unique cleavage site for the restriction enzyme PstI (codon 41/42) makes possible the sub-cloning of two gene fragments which can be incorporated in well investigated plasmids such as pUC18 or derivatives of these plasmids.

Additionally, a number of further unique recognition sequences for restriction enzymes can be incorporated within the structure gene, which on the one hand provide access to partial sequences of proinsulin and on the other hand permit mutations to be carried out:

| Restriction enzyme | Cut after nucleotide no. (encoding strand) |
|---|---|
| AccI | 201 |
| DraIII | 46 |
| FnuDII | 107 |
| HgaI | 105 |
| HindIII | 213 |
| HinfI | 17 |
| HpaI | 22 |
| HphI | 76 |
| MaeI | 155 |
| MaeIII | 191 |
| MboII | 89 |
| MluI | 106 |
| NcoI | 207 |
| NlaIII | 208 |
| PvuII | 175 |
| SalI | 201 |
| SpeI | 154 |
| StyI | 207 |
| TaqI | 202 |

The DNA sequence I was modified from the natural sequence at essential points. In this way, the insertion of the numerous unique cleavage sites for restriction enzymes was possible.

The DNA sequence I can be constructed from a total of 6 oligonucleotides having a chain length of 47 to 96 nucleotide units. For this purpose, the procedure is as described in the following.

The gene fragment IK I (Table 1) can be constructed from 4 oligonucleotides having a chain length of 47 to 74 units by first synthesizing these chemically and then linking them enzymatically via "sticky ends" of 3 nucleotides. The sticky ends correspond to those of the restriction enzyme DraIII, which is advantageous for later modifications.

The gene fragment IK II (Table 2) can be obtained from two chemically synthesized oligonucleotides having a length of 88 and 96 nucleotide units.

EXAMPLES

The numbers in parentheses in the specification, such as (1), (2), etc. correspond to the DNA fragments in the Figures and Tables of the specification, marked with the same designations. The numbered oligonucleotide fragments, such as oligonucleotide No. 4, refer to those single stranded DNA segments in the Tables, marked with dashed lines extending on both sides of each number and delimited by arrowheads pointing in opposite directions.

Example 1
a) Chemical Synthesis of a Single-stranded Oligonucleotide

The synthesis of the DNA building blocks is explained using oligonucleotide No. 4 (Table 1) as an example. For the solid phase synthesis, the nucleoside at the 3' end, i.e. adenine (nucleotide No. 125) in the present case, is used bonded covalently to a support via the 3'-hydroxyl function. The support material is CPG ("controlled pore glass") functionalized with long-chain aminoalkyl radicals.

In the following synthetic steps, the base component is employed as β-cyanoethyl N,N'-dialkyl-5'-O-dimethoxy-tritylnucleoside-3'-phosphoramidite, where the adenine is present as the $N^6$-benzoyl compound, the cytosine as the $N^4$-benzoyl compound, the guanine as the $N^2$-isobutyl compound and the thymine without a protective group.

25 mg of the polymeric support, which contains 0.2 μmol of 5'-O-dimethoxytrityl-$N^4$-benzoyl-2'-desoxyadenosine bonded, are successively treated with the following agents:
A) acetonitrile
B) 3% trichloroacetic acid in dichloromethane
C) acetonitrile
D) 5 μmol of the appropriate nucleoside-3'-O-phosphite and 25 μmol of tetrazole in 0.15 ml of anhydrous acetonitrile
E) acetonitrile
F) 20% acetic anhydride in tetrahydrofuran containing 40% lutidine and 10% dimethylaminopyridine
G) acetonitrile
H) 3% iodine in lutidine/water/tetrahydrofuran in a volume ratio of 5:4:1

In this connection, "phosphite" is taken to mean β-cyanoethyl 2'-desoxyribose-3'-monophosphite, the third valency being satisfied by a diisopropylamino radical. The yields of the individual synthesis steps can in each case be determined spectophotometrically by the detritylation reaction B) by measuring the absorption of the dimethoxytrityl cation at the wavelength of 496 nm.

After synthesis has been concluded, the cleavage of the dimethoxytrityl group is carried out as described in A) to C). The oligonucleotide is cleaved from the support by treatment with ammonia and the β-cyanoethyl groups are eliminated at the same time. The amino protective groups of the bases are cleaved quantitatively by treatment of the oligomers with concentrated ammonia at 50° C. for 16 hours. The crude product thus obtained is purified by polyacrylamide gel electrophoresis.

The oligonucleotides 1–3 (Table 1), 5 and 6 (Table 2) are prepared in an analogous manner.

b) Enzymatic Linkage of the Single-stranded Oligonucleotides

For enzymatic phosphorylation of the oligonucleotides at the 5' terminus, each 1 μmol of the oligonucleotides 1 and 4 is treated for 30 minutes at 37° C. with four units of T4 polynucleotide kinase in 20 μl of 50 mM tris-HCl buffer (pH 7.6), 10 mM of magnesium chloride and 10 mM of dithio-threitol (DTT). The enzyme is inactivated by heating to 95° C. for 5 minutes. The oligonucleotides 2 and 3, which form the "protruding" single-stranded sequences, are not phosphorylated. This prevents the formation of larger gene fragments in the subsequent ligation.

The oligonucleotides 1 to 4 are ligated as follow: each 1 μmol of the oligonucleotides 1 and 2 or 3 and 4 are hybridized in pairs by dissolving these in each case in 20 μl of 50 mM tris-HCl buffer (pH 7.6), 10 mM of magnesium chloride and 10 mM of DTT, heating this solution to 95° C. for 5 minutes and cooling to room temperature within 2 hours. For this purpose, the oligonucleotides 1 and 4 are employed in the form of their 5'-phosphates. For further linking of the bihelical DNA fragments formed, the solutions of these are combined, warmed to 60° C. for 15 minutes and cooled to room temperature. 2 μl of 0.1 M DDT, 16 μl of 2.5 mM adenosine triphosphate (pH 7) and 1 μl of T4 DNA ligase (400 units) are then added and the mixture is incubated at 22° C. for 16 hours.

The purification of the gene fragments thus obtained (Tables 1 and 2) is carried out by gel electrophoresis on a 10% strength polyacrylamide gel (without addition of urea, 40×20×0.1 cm), ΦX174 DNA (BRL) cleaved using HinfI, or pBR322, cut using HaeIII, being used as a labeling substance.

Example 2 a) Cloning of the Synthesized DNA Fragments

The commercial plasmid pUC19 is opened using the restriction enzymes KpnI and PstI and the large fragment (1) is separated through a 0.8% strength "Seaplaque" gel. This fragment is reacted with T4 DNA ligase using the DNA (2) synthesized according to Table 1 and the ligation mixture is incubated with competent E. coli 79/02 cells. The transformation mixture is plated out on IPTG/Xgal plates which contain 20 mg/l of ampicillin. The plasmid DNA is isolated from the white colonies and characterized by restriction and DNA sequence analysis. The desired plasmids are called pIK1.

Accordingly, the DNA (5) according to Table 2 is ligated into pUC19 which has been opened using PstI and HindIII (4). The plasmid pIK2 (6) is obtained.

b) Construction of the Mini-proinsulin Gene

The DNA sequences (2) and (5) according to Table 1 and 2 are reisolated from the plasmids pIK1 (3) and pIK2 (6) and ligated with pUC19, which has been opened using KpnI and HindIII (7). The plasmid pIK3 (8) is thus obtained which encodes for a modified human insulin sequence.

The plasmid pIK3 (8) is opened using MluI and SpeI and the large fragment (9) is isolated. This is ligated with the DNA sequence (10)

```
           B30      A1  A2  A3  A4  A5  A6  A7  A8    A9

(Thr)   (Arg) Gly Ile Val Glu Gln Cys Cys (Thr) (Ser)  (10)

5'    CG     CGT  GGT ATC GTT GAA CAA TGT TGT  A           3'

3'            A   CCA TAG CAA CTT GTT ACA ACA  TGA    TC   5'

(MLUI)                                                (SpeI)
``` which supplements the last codon of the B chain (B30) by one arginine codon and replaces the excised codon for the first 7 amino acids of the A chain and supplements the codon for the amino acids 8 and 9 of this chain.

The plasmid pIK4 (11) is thus obtained, which encodes for the human mini-proinsulin according to the invention.

c) Expression Vectors for Mini-proinsulin pIK I:

The plasmid pK50 (12) known from EP-A 0,229,998 (Example 3 therein; FIG. 3 (33)) is cleaved using EcoRI and HindIII. Both fragments (13) and (14) are isolated. The small fragment (14) containing the IL-2 partial sequence is subsequently cleaved with MluI and the IL-2 partial sequence (15) is isolated.

The plasmid pIK4 (11) is cleaved using EcoRI and HpaI and the large fragment (16) is isolated. This is now ligated with the IL-2 partial sequence (15) and the synthetic DNA (17)

the plasmid pIK8 (18) being obtained. This encodes for a fusion protein in which a bridging member Met-Ile-Glu-Gly-Arg and then the amino acid sequence of the mini-proinsulin follow the first 38 amino acids of the IL-2.

The EcoRI-HindIII fragment which encodes for the fusion protein mentioned is excised from the plasmid pIK8 (18). This fragment is ligated with the large fragment (13) which was obtained in the cleavage of pK50. The expression vector pIK10 (20) which encodes for the previously characterized fusion protein is thus obtained.

pSW3:

If the NdeI-BstEII segment which includes the "bom site" in removed from the vector pIK10 (20), a vector is obtained which is present in the cell in a relatively high copy number and—on account of the missing "bom site"—can no longer be mobilized by conjugative plasmids.

For this purpose, the vector pIK10 (20) is cleaved using BstEII and NdeI, which is precipitated using ethanol, tranferred in DNA polymerase buffer and subjected to a Klenow polymerase reaction. The truncated DNA fragments thus formed are separated by gel electrophoresis and the larger fragment (21) is isolated. The vector pSW3 (22) is obtained by ligation. After transformation of competent E. coli-Mc1061 cells and amplification, the plasmid pSW3 (22) is isolated and characterized.

Example 3
Expression in the Strain E. coli W3110

An overnight culture of E. coli cells which contain the plasmid pIK10 (20) or pSW3 (22) is diluted in a ratio of about 1:100 using LB medium (J. H. Miller, Experiments in Molecular Genetics, Cold Spring Harbor Laboratory, 1972) which contains 50 µg/ml of ampicillin and the growth is followed by means of OD measurement. At OD=0.5, the culture is adjusted to 1 mM IPTG and the bacteria are centrifuged off after 150 to 180 minutes. The bacteria are boiled for 5 minutes in a buffer mixture (7 M urea, 0.1% SDS, 0.1 M sodium phosphate, pH 7.0) and samples are applied to an SDS gel electrophoresis plate. After analysis by gel electrophoresis, an additional band is observed in the region from about 10 Kd, which corresponds to the fusion protein expected. This band reacts with antibodies directed against insulin in the "Western Blot" experiment. If the cells are disintegrated under pressure and the debris is centrifuged off, the fusion protein is found in the sediment in addition to other insoluble cell constituents.

The induction conditions indicated apply to shaken cultures; with larger fermentations the choice of other media and conditions, for example in order to obtain changed O.D. values, is expedient.

Example 4
a) Preparation of Mono-Arg Insulin 40 g of the fusion protein concentrated by centrifugation and washing with phosphate buffer (pH 7) or water (dry substance content about 25%) are dissolved in 75 ml of 98–100% strength phosphoric acid and 5 g of BrCN are added. After reacting for 6 hours at room temperature, 2 l of water are added to the mixture and it is freeze-dried.

The fragment mixture (10 g) is dissolved in 1 l of buffer solution (8 M urea, 0.2 M tris-HCl (pH 8.5)), warmed to 30° C. and 10 g of sodium sulfite and 2.5 g of sodium tetrathionate are added. After 90 minutes at 30° C., 3 l of cold water are added and the pH is adjusted to 7.0. The resulting precipitate is centrifuged off. The hexa-S-sulfonate of the mini-proinsulin is precipitated from the supernatant by adjusting the pH to 3.5. The mixture is centrifuged after incubating for 15 hours at +4° C. The precipitate is washed with 200 ml of water and freeze-dried. 4.8 g of a substance mixture in which a mini-proinsulin content of 900 mg is determined by RP-HPLC are obtained. The concentration of the S sulfonate is carried out in two steps:

1. Anion exchange chromatography through a 5×60 cm column containing ®Fractogel TSK DEAE 650 M in 3 M urea; 0.05 M tris-HCl (pH 8.3). The elution is performed using a gradient of 0.05–0.5 M NaCl (each 6 l). After analysis of the eluate by isoelectric focusing, the product is precipitated from the combined fractions by diluting to 1 M urea and adjusting the pH to 3.5.

2. Removal of high and low molecular weight impurities by gel filtration through ®Sephacryl S200 in 3 M urea; 0.05 M tris-HCl; 0.05 M NaCl (pH 8.3). Analysis of the fractions and isolation of the product are carried out as in the preceding step. The precipitate is washed with 20 ml of water and freeze-dried. 1.10 g of product cocentrated to 69% purity are obtained.

For folding and disulfide bridge formation, the S sulfonate is dissolved in 50 ml of 8 M urea; 0.02 M tris-HCl at pH 8.6. After addition of a few drops of octanol, purified nitrogen is passed into the mixture for 15 minutes. Complete reduction is carried out in the course of 1 hour at room temperature by addition of 1.1 ml (16 mMol) of 2-mercaptoethanol. The solution is applied to a ®Sephadex G25 column (5×60 cm) and eluted using 0.05 M glycine/NaOH (pH 10.6). The protein fraction in 300 ml of the glycine buffer is kept for 2 days at 4° C. after checking and, if necessary, correction of the pH value (10.6). The solution is then adjusted to a pH of 6.8 and the solution is incubated at room temperature for 4 hours with 1 mg (3.5 U) of trypsin (Merck, treated with L-1-p-tosylamino-2-phenylethylchloromethyl ketone (TPCK). The pH is then adjusted to 3.5, 1 mg of soya bean trypsin inhibitor (Sigma) and 3 ml 10% $ZnCl_2$ are added and the solution is readjusted again to pH 6.8. The resulting precipitate is separated by centrifugation. It contains predominantly mono-Arg insulin which is purified by ion exchange chromatography on S-Sepharose® (2.5×40 cm) in a buffer composed of 50 mM lactic acid and 30% isopropanol (pH 3.5). Elution is carried out by means of a gradient of 0.05–0.50 M of NaCl (each 1 l). The elutate is analyzed by HPLC; the mono-Arg insulin is precipitated from the product-containing fractions after 1:1 dilution with $H_2O$ by adding 10 ml of 10% $ZnCl_2$ per 1 l and adjusting the pH to 6.8. The precipitate separated by centrifugation is crystallized at pH 6 from a buffer composed of 1 g/l of phenol, 10.5 g/l of citric acid and 200 mg/l of $ZnCl_2$. 390 mg of mono-Arg insulin in over 90% purity are obtained after freeze-drying the crystals washed with some water.

Example 5
Preparation of Insulin 200 mg of mono-Arg insulin (see Example 4) are dissolved in 100 ml of 0.05 M tris-HCl (pH 8.5). 1 U (about 4 µg) of carboxypeptidase B is then added and the solution is stirred slowly at room temperature. After 3 hours, the human insulin is crystallized by acidifying to pH 3.5 and adding 1 ml of 10% $ZnCl_2$ at pH 5.5. 200 mg of crystalline insulin having a purity of more than 85% are obtained. This material is subjected to purification by ion exchange chromatography on a column containing Fractogel TSK DEAE 650 M (2.5×40 cm) in 0.1% ® Lutensol ON 100 (BASF AG; oxethylate of a linear saturated fatty alcohol of essentially 12 carbon atoms); 0.05 M tris-HCl (pH 8.3), the elution being carried out using a gradient of 0–0.4 M NaCl (each 1 l). The insulin is crystallized at pH 5.5 from the product-containing fractions identified by means of HPLC after addition of 10 ml of 10% $ZnCl_2$ and 1 ml of 10% citric acid. After slowly stirring overnight, the mixture is centrifuged and the sediment obtained is recrystalized at pH 5.5 from 20 ml of a buffer composed of 5 g/l of citric acid, 125 ml/l of acetone and 200 mg/l of $ZnCl_2$. 160 mg of insulin having a purity of more than 95% are obtained.

Example 6

Construction of a Yeast Expression Vector

The DNA sequence (23) (Table 3) is first synthesized by the phosphite method. This DNA sequence (23) encodes for the amino acids 49 to 80 of the MFα precursor protein and corresponds essentially to the natural DNA sequence.

The DNA sequence (23) is first used as a probe for the isolation of the gene for the a factor and is labeled with $^{32}P$ for this purpose. With the aid of this probe, the gene is isolated from a genomic λgt11 yeast gene bank. (as are meanwhile commercially available and obtainable, for example, at Clontech Laboratories Inc., 4055 Fabian Way, Palo Alto, Calif. 94303). To this end, λgt11 phages which carry the α factor gene are identified in a plaque hybridization experiment. Phages from plaques identified as positive are isolated, replicated and the DNA obtained. This is cleaved using EcoRI and analyzed on a 0.8% strength agarose gel. The membrane is hybridized against the $^{32}P$-labeled DNA sequence (23) by a "Southern transfer" experiment. Phage DNA which contains a fragment of about 1.75 kb (24) which is hybridized against the DNA sequence (23) is again cleaved with the enzyme and the corresponding fragment (24) is isolated. The vector pUC 19 is opened using EcoRI (25) and reacted with the 1.75 kb fragment (24) using T4 ligase. The cloning vector (26) is obtained.

The strain E. coli 79/02 is transformed using the ligation mixture. White colonies are isolated, the plasmid DNA is obtained from these and plasmids (26) which contain the 1.75 kb EcoRI fragment, are identified.

The natural DNA sequence of the precursor protein for MFα contains a PstI cleavage site in the region of amino acids 8 to 10 and a TaqI cleavage site in the region of amino acids 48/49. From the isolated plasmid DNA (26), the fragment (27) which encodes for the amino acids 9 to 48 of the MFα precursor sequence is isolated by reaction with PstI and TaqI. The vector pUC18 is opened using PstI and KpnI and reacted with the PstI-TaqI fragment (27) and with the synthetic DNA sequence (23) with the aid of T4 ligase. E. coli 79/02 is transformed using the ligation mixture. The transformation mixture is plated out on to IPTG-Xgal-Ap-plates. White colonies are a isolated and the plasmid DNA of this clone is characterized by restriction analysis. The cloning vector (29) which encodes for the amino acids 8 to 80 of the MFα precursor sequence is thus obtained.

The encoding sequence (30) mentioned is excised from the cloning vector (29) by reaction with PstI and KpnI and incorporated in the ligation described in the following. For this purpose, the cloning vector (26) is reacted with EcoRI and partially with PstI and the fragment (31) including the encoding sequence for the first 8 amino acids of the MFα precursor sequence is isolated. Furthermore, the vector pUC19 is opened using EcoRI and KpnI (32) and ligated with the two fragments (30) and (31) described, the cloning vector (33) being form d. This encodes for the total precursor sequence of MFα up to amino acid 80.

Figure 2A:
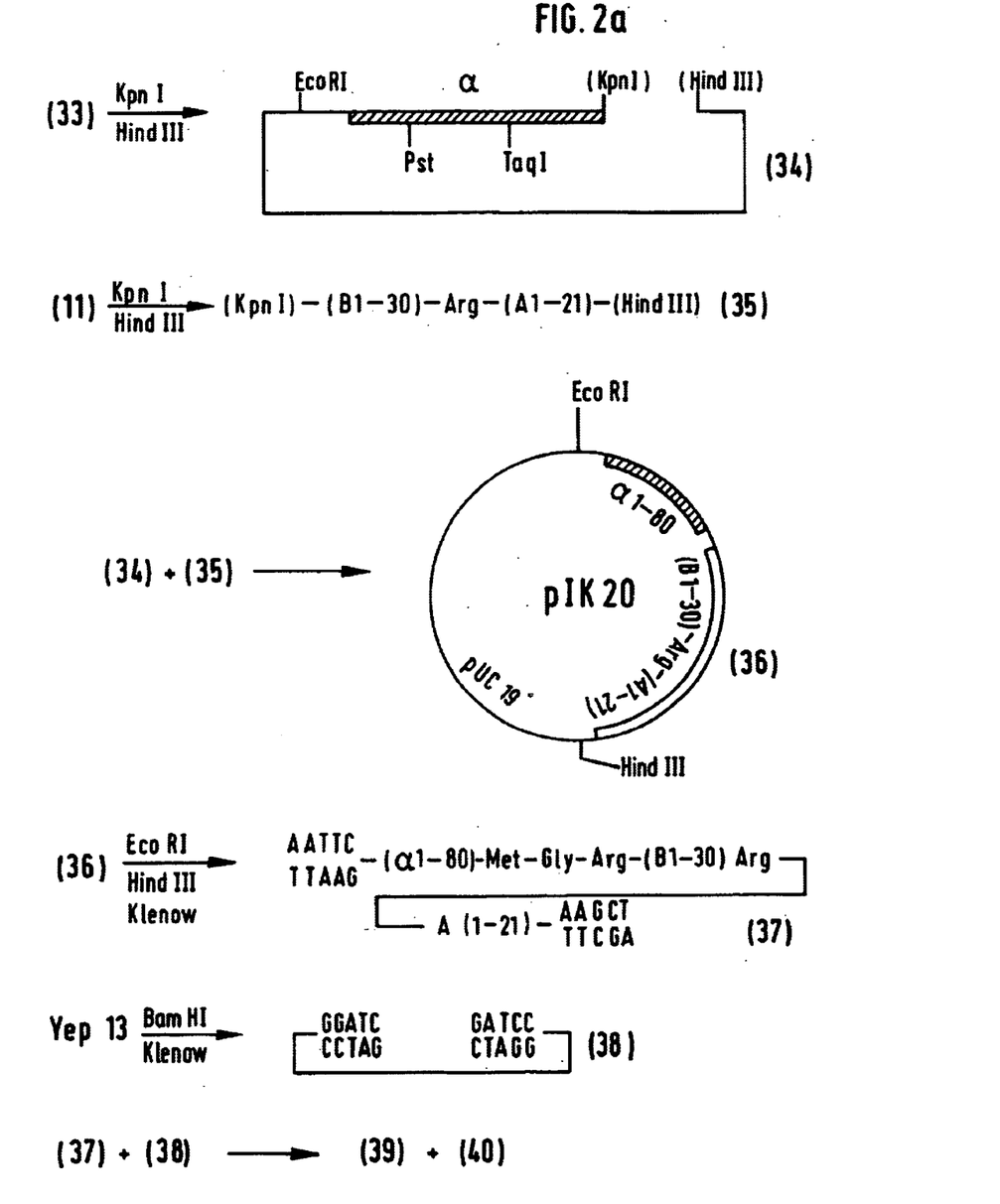

The cloning vector (33) is opened using KpnI and HindIII and the large fragment (34) is isolated. This is ligated using the KpnI-HindIII fragment (35) from the plasmid (11) which encodes for the mini-proinsulin. The plasmid pIK20 (36), the structure of which is confirmed by restriction analysis, is thus obtained.

The plasmid Yep13 (Broach et al., Gene 8 (1979) 121) is opened using BamHI and the protruding ends are filled in with Klenow polymerase (38). The DNA is precipitated using ethanol and treated with alkaline bovine phosphatase.

The fragment encoding for the insulin derivative and the precursor sequence of MFα is excised from the cloning vector (36) using HindIII and EcoRI and the protruding ends are filled in as described (37).

Figure 2B:
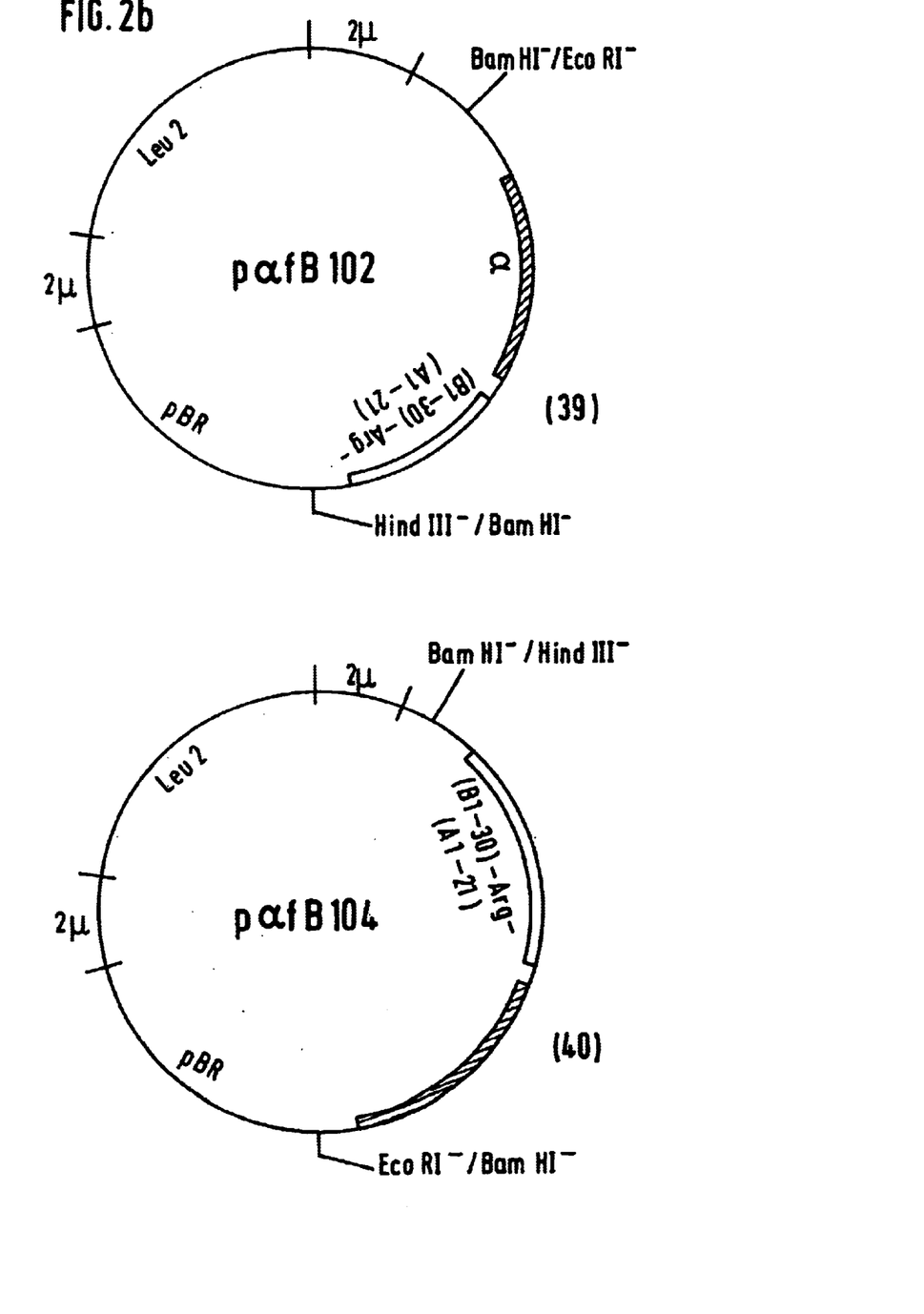

The two truncated DNA sequences (37) and (38) are ligated with one another, the plasmids pαfB102 (39) and pαfB104 (40) being formed. These two plasmids differ only in the orientation of the inserted fragment.

As described in EP-A 0,171,024, a terminator can be inserted behind the Inserted sequence (FIGS. 4 to 6 of EP-A 0,171,024). For this purpose, the NcoI and/or the BamHI cleavage sites are suitable.

After amplification of the plasmid DNA in E. coli MM294, the plasmid pαfB102 (39) is transformed in the leucine-requiring yeast strain Y79 (α,trp1,leu2-1) (Cantrell et al., Proc. Acad. Natl. Sci. USA 82 (1985) 6250) and DM6-6 (α/α leu2–3,112::ura3$^+$/leu2::lys2$^+$, trp1$^-$/trp1$^-$, his3–11, 15/his3–11, 15, ura3$^-$/ura3$^-$, lys2$^-$/lys2$^-$, arg4–17/arg4$^+$, ade1/ade1$^+$) (Maya Hanna, Dept. Mol. Biol. Massachusetts General Hospital, Boston, USA) by the lithium method of Ito, H. et al., J. Bacteriol., 153 (1983) 163. Colonies which can grow on selective medium without addition of leucine, are isolated and combined. Yeast minimum medium is inoculated with the individual colonies and incubated at 28° C. for 24 hours. The cells are centrifuged off and the supernatant is tested for insulin activity in an RIA test. The plasmid DNA is reisolated from yeast clones whose supernatant shows insulin activity, and characterized by restriction analysis. The transformed yeast strains are employed for the following expression.

Example 7

Expression in Yeast 10 ml of yeast complete medium is inoculated with cells which have been removed from a fresh overnight culture of a strain of selective medium obtained according to Example 7, in such a way that an optical density $OD_{600}$=0.1 is achieved. The culture is shaken at 28° C. for 8 hours, after which 90 ml of fresh medium are added. The culture is then shaken for a further 20 hours. The cells are centrifuged off and the insulin concentration is determined in the supernatant. The conditions are modified for a larger fermentation, for example fresh medium can be added continuously.

Example 8

Purification of Mono-Arg Insulin from Yeast Supernatant

The fermentation supernatant is added through an adsorption column containing a porous adsorber resin composed of a copolymer of styrene and divinylbenzene (®Diaion HP 20). The column was previously equilibrated with a 20–50 mM acetate buffer (pH 5). After washing with tris buffer (pH 8), an isopropanol gradient (0–50%) is applied using a 10-fold column volume. Insulin-containing fractions are adjusted to pH 6, ®MATREX CELLUFINE AM (Amicon) is added, and the mixture is stirred and filtered off with suction and washed with 50 mm acetate buffer (pH 6). The wash fraction and the main fraction are combined, adjusted to pH 3.5 using lactic acid and added through an S-SEPHAROSE column which has been equilibrated using 50 mM lactic acid (pH 5)/30% isopropanol.

The elution is carried out by means of a 0–0.6 N NaCl gradient. Mini-proinsulin elutes in the range 0.25–0.3 M.

The proinsulin-containing fractions are concentrated to ¼ of the volume and added through a column containing Biogel P10 (Bio-Rad), equilibrated in 6% acetic acid (pH 2). The insulin-containing eluate is lyophilised and purified through a preparative "reversed phase" HPLC step (RP18 material, 0.1% TFA, acetonitrile gradient 20–40%). After subsequent freeze-drying, the lyophilisate is dissolved in tris buffer (pH 6.8) and incubated for 3 to 5 hours at room temperature with 4 units of trypsin per gramme of mono-Arg proinsulin. The course of the reaction is checked by "reversed-phase" analysis. It shows that mono-Arg insulin is formed nearly quantitatively. At the end of the reaction, the pH is adjusted to 3.5 and the reaction is completed by addition of an equivalent amount of trypsin inhibitor. The zinc chloride concentration is then adjusted to 0.21 g/l and the pH to 6.8. A flocculent precipitate is obtained which is dissolved in lactic acid buffer. The components are separated from one another by means of S-SEPHAROSE chromatography. Fractions which contain mono-Arg insulin are combined and mixed with water in the ratio 1:1. 10 ml of 10% $ZnCl_2$ per 1 l are then added to the solution. Mono-Arg insulin then precipitates at pH 6.8 and is recrystallized in a known (for insulin) manner.

Example 9
Preparation of Human Insulin

The mono-Arg insulin prepared according to Example 9 is used as a starting substance for the carboxypeptidase B cleavage. To this end, the insulin derivative is dissolved in tris buffer (pH 8.5) and 5 units of carboxypeptidase per gramme of mono-Arg insulin are added. The reaction is carried out over the course of 3 hours with slow stirring at room temperature. The product is then precipitated with $ZnCl_2$ as described in Example 9. Human insulin is then purified in a known manner (DE-B 2,629,568).

Example 10
Preparation of Insulin from Mini-proinsulin by Combined use of Trypsin and Carboxypeptidase B 5 mg of mini-proinsulin are dissolved in 20 ml of 0.1 M of tris-HCl (pH 8.0) and the solution is warmed to 30° C. At the same time, 2.5 µl of trypsin solution (1 U/ml) and 150 µl of carboxypeptidase B solution (1 U/ml) are added. After 3 hours, the solution is adjusted to pH 3.5 and 2.5 µl of trypsin inhibitor solution (1 U/ml) and 200 µl of 10% strength $ZnCl_2$ solution are added. The human insulin is precipitated by adjusting to pH 6.8, centrifuged off and crystallized as in Example 5. The crystallized insulin has a purity >95%.

TABLE 1

Gene fragment IK I (2)

```
                       B¹
                       Phe
            10         20         30         40
             •          •          •          •

<-------------------------2---------------------------
        CT TTG GAC AAG AGA TTC GTT AAC CAA CAC TTG TGT GGT TCT CAC
    CAT GGA AAC CTG TTC TCT AAG CAA TTG GTT GTG AAC ACA CCA AGA GTG
        <-------------------------1------------------------->
    (KpnI)                      HpaI 50         60         70         80         90
       •          •          •          •          •

-->  <----------------------------------------------4--------
    TTG GTG GAA GCG TTG TAC TTG GTT TGT GGT GAG CGT GGT TTC TTC
    AAC CAC CTT CGC AAC ATG AAC CAA ACA CCA CTC GCA CCA AAG AAG
         <---------------------------------------------3------------

B³⁰
                       Thr Arg Lys Gly Ser Leu
            100        110        120
             •          •          •

---------------------------------------->
    TAC ACT CCA AAG ACG CGT AAG GGT TCT CTG CA
    ATG TGA GGT TTC TGC GCA TTC CCA AGA G
         ---------------------------------->
                       MluI       (PstI)
```

TABLE 2

Gene fragment IK II (5)

```
                   A¹
            Gln Lys Arg Gly
                 130        140        150        160
                  •          •          •          •

<-----------------------------------------------------6
          G AAG CGT GGT ATC GTT GAA CAA TGT TGT ACT AGT ATC TGT TCT
         AC GTC TTC GCA CCA TAG CAA CTT GTT ACA ACA TGA TCA TAG ACA AGA
              <-----------------------------------------------------5
          (PstI)                                              SpeI

A²¹
                            Asn
             170        180        190        200        210
              •          •          •          •          •

------------------------------------------------------->
```

TABLE 2-continued

Gene fragment IK II (5)

```
TTG TAC CAG CTG GAA AAC TAC TGT AAC TGA TAG TCG ACC CAT GGA
AAC ATG GTC GAC CTT TTG ATG ACA TTG ACT ATC AGC TGG GTA CCT TCG A
                                                     ------------>
                                                        (HindlII)
```

TABLE 3

DNA sequence (23)

```
              50                    55
    5'    C GAT GTT GCT GTT TTG CCA TTC TCC
    3'      TA CAA CGA CAA AAC GGT AAG AGG
        (TaqI)
                   60                    65
        AAC AGT ACT AAT AAC GGT TTA TTG TTC
        TTG TCA TGA TTA TTG CCA AAT AAC AAG
                        70
        ATT AAT ACT ACT ATT GCT AGC ATT GCT
        TAA TTA TGA TGA TAA CGA TCG TAA CGA
        75                80
        GCT AAA GAA GAA GGG GTA C      3'
        CGA TTT CTT CTT CCC            5'
                        (KpnI)
```

What is claimed is:

1. A method for the preparation of a mono-Arg-insulin compound of formula II (II)

in which A(1–21) and B(1–30) denote the A and B chains of human insulin and the -S-S-bridges are positioned as in insulin, which comprises:
   (a) expressing in a bacterium a DNA molecule encoding a fusion protein which comprises a mini-proinsulin compound of the formula:

B(1–30)-Arg-A(1–31);

(b) liberating said mini-proinsulin compound from said fusion protein;
   (c) folding and forming disulfide bridges in said mini-proinsulin compound;
   (d) incubating said mini-proinsulin compound with trypsin; and
   (e) precipitating the mono-Arg-insulin.

2. A method for the preparation of insulin which comprises:
   (a) expressing in a bacterium a DNA molecule encoding a fusion protein which comprises a mini-proinsulin compound of the formula:

B(1–30)-Arg-A(1–21), in which B(1–30) and A(1–21) denote the B and A chains of insulin;
   (b) liberating said mini-proinsulin compound from said fusion protein;
   (c) folding and forming disulfide bridges in said mini-proinsulin compound;
   (d) simultaneously incubating said mini-proinsulin compound with trypsin and carboxypeptidase B; and
   (e) precipitating the insulin.

3. A method as claimed in claim 2, wherein step (d) is carried out in one vessel without having to isolate as an intermediate mono-Arg-insulin of formula II 4. A method for the preparation of a mono-Arg-insulin compound of formula II in which A(1–21) and B(1–30) denote the A and B chains of human insulin and the -S-S-bridges are positioned as in insulin, which comprises:
   (a) expressing in a bacterium a DNA molecule encoding a fusion protein which comprises B(1–30)-Arg-A(1–21)

bonded via a bridging member,

-Met-Ile-Glu-Gly-Arg-, to a peptide which stabilizes the fusion protein;
   (b) liberating a mini-proinsulin compound from said fusion protein by cleaving the expressed fusion protein resulting from step (a) with cyanogen bromide;
   (c) folding and forming disulfide bridges in said mini-proinsulin compound;
   (d) incubating said mini-proinsulin compound with trypsin; and
   (e) precipitating the mono-Arg-insulin.

5. A method for the preparation of insulin which comprises:
   (a) expressing in a bacterium a DNA molecule encoding a fusion protein which comprises

B(1–30)-Arg-A(1–21)

bonded via a bridging member,

-Met-Ile-Glu-Gly-Arg-, to a peptide which stabilizes the fusion protein;
- (b) liberating a mini-proinsulin compound from said fusion protein by cleaving the expressed fusion protein resulting from step (a) with cyanogen bromide;
- (c) folding and forming disulfide bridges in said mini-proinsulin compound;
- (d) simultaneously incubating said mini-proinsulin compound with trypsin and carboxypeptidase B; and
- (e) precipitating the insulin.

6. A method as claimed in claim 5, wherein step (d) is carried out in one vessel without having to isolate as an intermediate mono-Arg-insulin of the formula II (II)

7. A method for the preparation of a compound of the formula II (II)

wherein A(1–21) and B(1–30) denote the A and B chains of human insulin and the -S-S-bridges are positioned as in insulin, comprising:
- a) expressing a DNA sequence encoding the compound of formula I

B(1–30)-Arg-A(1–21)    (I)

in a bacterium; and
- b) cleaving the expressed compound of step (a) with trypsin.

8. A method for the preparation of insulin comprising:
- a) expressing a DNA sequence encoding the compound of formula I B(1–30)-Arg-A(1–21)    (I)

in a bacterium;
- b) cleaving the expressed compound of step (a) with trypsin resulting in the compound of the formula II (II)

wherein A(1–21) and B(1–30) denote the A and B chains of human insulin and the -S-S-bridges are positioned as in insulin; and
- (c) cleaving the resulting compound of step (b) with carboxypeptidase B.

9. The method of claim 8, wherein steps (b) and (c) are carried out in one vessel without having to isolate the intermediate compound of the formula II.

(II)

10. A method for the preparation of a mono-Arg-insulin compound of the formula II (II)

in which A(1–21) and B(1–30) denote the A and B chains of human insulin and the -S-S-bridges are positioned as in insulin, which comprises:
- (a) expressing a DNA sequence encoding a mini-proinsulin compound of the formula:

B(1–30)-Arg-A(1–21)

in a yeast; and
- (b) cleaving said mini-proinsulin compound with trypsin.

* * * * *